United States Patent [19]

Jihad et al.

[11] Patent Number: 4,990,659

[45] Date of Patent: * Feb. 5, 1991

[54] PROCESS FOR THE MANUFACTURE OF DERIVATIVES OF BENZOIC ACID

[75] Inventors: Dakka Jihad; Zoran Amikam; Yoel Sasson, all of Jerusalem, Israel

[73] Assignees: Gadot Petrochemical Industries Ltd., Haira; Yissum Research Development Company of the Hebrew University, Jerusalem, both of Israel

[*] Notice: The portion of the term of this patent subsequent to Aug. 1, 2006 has been disclaimed.

[21] Appl. No.: 384,064

[22] Filed: Jul. 20, 1989

Related U.S. Application Data

[63] Continuation of Ser. No. 216,411, Jul. 7, 1988, abandoned.

[30] Foreign Application Priority Data

Jul. 23, 1987 [IL]  Israel ........................................ 83293
Apr. 5, 1988 [IL]  Israel ........................................ 85976

[51] Int. Cl.$^5$ ............................................. C07C 51/16
[52] U.S. Cl. ................................... 562/416; 562/417; 562/56; 562/414
[58] Field of Search .................. 562/414, 416, 417, 56

[56] References Cited

U.S. PATENT DOCUMENTS

| 2,865,708 | 12/1958 | Dinsmore | 562/414 |
| 2,883,816 | 4/1959 | Kroll | 53/244 |
| 3,210,416 | 10/1965 | Fragen | 562/414 |
| 3,227,752 | 1/1966 | Olivier | 562/412 |
| 3,665,030 | 5/1972 | deRadzitzkyd'Ostrowick | 260/488 |
| 3,816,523 | 6/1974 | Sidi | 562/414 |
| 4,007,223 | 2/1977 | Feld et al. | 260/524 R |
| 4,007,228 | 2/1977 | Feld | 260/524 |
| 4,853,479 | 8/1989 | Dakka et al. | 562/416 |

FOREIGN PATENT DOCUMENTS 1005315 9/1965 United Kingdom .

OTHER PUBLICATIONS

Sasson, J. Org. Chem., 51, pp. 2880–2883 (1986).
Chem. Abst., 93:71220c.

Primary Examiner—Michael L. Shippen
Attorney, Agent, or Firm—Morgan & Finnegan

[57] ABSTRACT

A process for the manufacture of benzoic acid derivatives is described. The process is based on the reaction of a toluene derivative in a liquid phase oxidation with an oxygen containing gas in the presence of a phase-transfer catalyst (a), a transition metal salt (b) and traces of a polar solvent, such as water, the molar ratio between (a) and (b) being in the range of between 0.25:1 to 1.5:1. The phase-transfer catalyst is selected from quaternary ammonium and phosphonium salts having a total carbon atoms in the range of 17 to 58, the anion bound thereto being selected from $Br^-$, $F^-$, $Cl^-$, $OH^-$, $CH_3COO^-$ or $HSO_4^{31}$. The benzoic acid derivatives produced are characterized by their very high purity and high conversion reaching generally values of above 95%.

22 Claims, No Drawings

PROCESS FOR THE MANUFACTURE OF DERIVATIVES OF BENZOIC ACID

This is a continuation of co-pending application Ser. No. 07/216,411, filed on July 7, 1988, now abandoned.

The present invention relates to a simple process for the manufacture of derivatives of benzoic acid and salts thereof. More particularly the invention relates to a simple process for the manufacture of derivatives of benzoic acid at high yield and purity from derivatives of toluene.

BACKGROUND OF THE INVENTION

The main procedure for the manufacture of derivatives of benzoic acid is based on the liquid phase oxidation with air or oxygen of derivatives of toluene in the presence of metallic catalyst(s). Among the most important derivatives of benzoic acid the following can be mentioned: ortho-and para halobenzoic acids, p-methoxybenzoic ,acid (p-anisic acid), p-phenyl benzoic acid, ortho-and para toluic acids, para-nitrobenzoic acid etc.

Catalysts which were found suitable for this oxidation are generally selected from salts of metals having variable valency such as chromium, cobalt, manganese, lead, iron, copper, nickel and vanadium. Also various compounds of cerium, selenium, silver, zinc and uranium were suggested.

In addition to the catalyst(s) sometimes a promoter is utilized generally being a bromine-affording substance such as elemental, or inorganic form. Typical examples of such promoters are sodium bromide, potassium bromide, ammonium bromide, manganese bromide or the like. The literature is quite abundant with various patents on processes for the manufacture of derivatives of benzoic acid.

According to U.K. Patent Number 1,005,315 (assigned to SNIA VISCOSA), para-toluic acid is obtained by the oxidation of para-xylene with an oxygen-containing gas in the presence of a special form of cobalt oxide catalyst containing 25-35% of oxygen. The catalyst is prepared by heating a cobalt salt or oxide in the dry state at temperatures in the range of 200-800° C. About 60% of the xylene was converted to p-toluic acid.

According to U.S. Pat. No. 4,007,223, p-nitrobenzoic acid is obtained by the oxidation of p-nitrotoluene with oxygen in an acetic acid reaction medium in the presence of a cobalt salt and a brominous compound (e.g.KBr, NaBr, and NH4Br) as catalysts, the amount of acetic acid being in the range of 3 to 15 moles per mole of p-nitrotoluene. It is claimed that in this manner a not discoloured p-nitrobenzoic acid is obtained at a conversion of 92-93% of the calculated product. Other related patents dealing with the subject of p-nitrobenzoic acid are U.S. Pat. Nos. 2,883,816 and 3,665,030.

In a theoretical review "Liquid-phase oxidation of deactivated methylbenzene by aqueous sodium hypochlorite catalyzed by ruthenium salts under phase transfer catalytic conditions" (Journal of Organic Chemistry, 1986, 51, 2880), there are presented some kinetic studies on the reaction in the presence of tetrabutyl ammonium bromide. Of course, the use of an aqueous solution of sodium hypochlorite as an oxidizing reagent is of little value from an industrial point of view.

It is an object of the present invention to provide a simple process for the manufacture of derivatives of benzoic acid and salts thereof from toluene derivatives. It is another object of the present invention to provide a simple process for the manufacture of derivatives of benzoic acid and salts thereof at high yield. It is yet another object of the present invention to provide a simple process for the manufacture of derivatives of benzoic acid of a high purity.

BRIEF DESCRIPTION OF THE INVENTION

The invention relates to a process for the manufacture of derivatives of benzoic acid from toluene derivatives—as defined in the specification—by a liquid phase oxidation of derivatives of toluene using an oxygen-containing gas, being carried out in the presence of a phase-transfer catalyst and traces of a polar solvent able to solubilize the catalyst, the process being characterized in that the oxidation reaction occurs in the presence of a catalytic system comprising:

(a) a quaternary onium salt having the general formula:

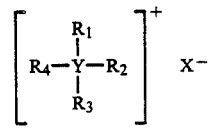

wherein $R_1$ is alkyl and $R_2$, $R_3$ and $R_4$ may be the same, different or interlinked, selected from alkyl, hydroxyalkyl, aryl or aralkyl group having a total number of carbon atoms in the range of 17 to 58, Y may be nitrogen or phosphorus and $X^-$ is selected from $F^-$, $Cl^-$, $Br^-$, $OH^-$, $CH_3COO^-$ and $HSO_4^-$ provided that when $Br^-$ is absent from the system a bromide or bromine is added; and (b) a transition metal salt, the molar ratio between (a) and (b) being in the range of between 0.25:1 to 1.5:1. The above quaternary onium salts, possessing between 17 and 58 carbon atoms, are characterized by their lipophilicity which enables the extraction of the transition metal salts.

The most preferable phase-transfer catalysts are the quaternary onium salts having between 20 and 48 total carbon atoms.

Typical examples of useful ammonium quaternary bromides and chlorides are: di-n-decyldimethyl ammonium bromide, tri-n-octylmethyl ammonium bromide, tetra-n-hexyl ammonium bromide, tetra-n-octyl ammonium bromide, tri-n-hexyl-2-hydroxyethyl ammonium bromide, phenyl-tri-n-octyl ammonium bromide, tetra-n-decyl ammonium bromide, tetra-n-dodecyl ammonium bromide, tetra-n-nonyl ammonium bromide, tetra-n-hexadecyl ammonium bromide, phenyl-tri-n-hexylammonium bromide, benzyl-tri-n-octylammonium bromide, phenyl-tri-n-decyl ammonium chloride, tri-n-dodecyl-2-hydroxyethyl ammonium chloride, n-hexadecylpyridinium bromide, etc. Most of these quaternary ammonium salts are also commercially available at reasonable costs. Among the quaternary phosphonium bromides and chlorides the following can be mentioned: tetra-n-hexylphosphonium bromide, tetra-n-octylphosphonium, bromide, phenyl-tri-n-hexylphosphomium chloride, n-hexadecyl-tri-n-butylphosphonium bromide, tetra-n-hexylphosphonium bromide, etc.

It was found that the iodide quaternary onium salts are substantially ineffective as phase-transfer catalyst for the process according to the present invention. It seems that in the presence of the transition metal salt the catalytic activity of the quaternary phosphonium iodide is greatly affected. Example 18 using quaternary phosphonium iodide, under the same conditions as in the present invention, clearly illustrates this matter. This is quite surprising and the inventors are not yet in a position to explain this anomaly.

In the German Patent No.1,263,003 it is claimed a process for the catalytic oxidation of hydrocarbons at a temperature in the range of 0 to 250° C. using phosphonium quaternary salts. The presence of acetic acid is mentioned to be optionally required in view of the high pressure prevailing in the system. In the example for the oxidation of xylene, the iodide phosphonium salt is utilized in the presence of a large amount of acetic acid (10 times on the amount of xylene). From the Examples given it appears that yields in the range of about 35% to 70% were obtained. The mechanism involved in this oxidation seems to be based on the activation of the phosphonium catalyst in the reaction system. It was found that the corresponding phosphonium iodide salt gave under the conditions of the present invention only poor conversions of about 5 to 10%.

Other phase-transfer catalysts which may be used are for example, crown ethers (macrocyclic polyethers) which are described in detail in the "Journal of the American Chemical Society", 89, 7017 (1967).

The transition metal to be used in the catalytic system is selected from manganese, cobalt, molybdenum, chromium, vanadium, tungsten, cerium or mixtures thereof Most preferred are chromium and cobalt. The amount of transition metal salt can be selected in a very broad molar ratios range such as between 1:1000 to 1:100 (transition metal salt to the toluene) and preferably between 1:500 to 1:200. The transition metal salt is preferably in the hydrated form containing water of crystallization.

The anion to which the heavy metal is bound, is not critical and may be selected from any inorganic or organic moiety provided that the corresponding salt can be solubilized in the reaction system. Particularly preferable are acetates, chlorides, sulfates, which are also commercially available in bulk.

The oxidation may be carried out with pure oxygen gas or preferably with a gaseous mixture containing lower concentrations of oxygen such as, for example air.

The phase-transfer catalyst has a very important role in the process according to the present invention. As known, a phase-transfer catalyst is defined as a substance which promotes reaction by transferring a substance from one phase to another phase where it undergoes the desired reaction thereby releasing the phase-transfer catalyst back into the first phase for re-use. According to the present invention it was found that the heavy metal salt is solubilized in the organic phase in the form of an onium adduct. In this manner, it catalyses the oxidation reaction.

The quaternary onium salt may be added such as, or prepared in-situ for example, in case of ammonium salt by including in the reaction system a tertiary amine and an alkylating agent.

In order to initiate the reaction, the process according to the present invention must involve the addition of traces of a polar solvent such as minor of water, preferably present with the metal salt in the form of water of crystallization. The amount of polar solvent should be sufficient to dissolve the metal salt as a saturated solution under the reaction conditions. It has been found that an increase in the amount of water in the system decreases the reaction rate and generally should be avoided.

The term of toluene derivatives as used in the present specification means: alkyl toluenes (linear or branched), aryl toluenes, aralkyl toluenes, halo-toluenes, nitrotoluenes, alkoxy toluenes, aryl-oxy toluenes and combinations thereof as well as sulfonated toluenes. Typical examples of such toluene derivatives are ortho- and paraxylene, p-nitro toluene, p-methyl biphenyl, p-methoxy toluene, chlorotoluenes, bromotoluenes, etc.

The process according to the present invention is characterized by its very high yield generally of above 90% and even above 99%. It was also found that the derivatives of benzoic acid produced are substantially pure containing only minor amounts of by-products usually encountered in the prior art methods. In this manner, additional purification steps will be significantly reduced for certain applications.

The invention is particularly useful for the oxidation of derivatives of toluene into benzoic acid derivatives. However, one may conceive to start with oxidation products of toluene derivatives.

It was surprisingly found that the yield of the toluene derivatives into benzoic acid derivatives, is correlated to the molar ratio between the phase-transfer catalyst (a) and the transition metal salt (b). It was found, that conversion of above 60% are obtained when said ratio is about 0.35, reaching above 90% when said molar ratio (a):(b) is about 0.8. Above this ratio, there is a sudden decrease in the conversion rate which can reach even a value close to zero when the above ratio is about 2:1. The molar ratio of (a):(b) to be used in the process according to the present invention is in the range of between 0.25:1 to 1.5:1 and preferably 0.4:1 to 1.15:1.

The use of bromide ion as a promoter in the liquid phase oxidation of xylene is indeed mentioned in the prior art. However, the use of a bromide ion leads to corrosion of the apparatus by the resulted bromine and will impose corrosion-resistant equipment. According to the present invention, using the bromide ion bound to the quaternary onium moiety, or becomes bound to the quaternary onium moiety, this problem is substantially reduced in view of the absence of an aqueous phase.

The oxidation reaction according to the present invention is carried out either batchwise or continuously at an elevated temperature in the range of 100 to 200° C. and preferably in the range of 120 to 170° C. Also, elevated pressure will be required e.g. in the range of 1 to 60 atmospheres (air) and generally about 10 to 25 atmospheres, corresponding to an oxygen partial pressure in the range of 2 to 5 atmospheres.

The reaction may be carried out also in the presence of a solvent. The solvent should be inert at the reaction conditions. A preferred solvent might be the toluene derivative reactant, used as starting material, in which case it will be separated from the final product and recycled to the process. A typical example for this embodiment is the preparation of p-nitrobenzoic acid, wherein the p-nitrotoluene—the starting raw material serves as the solvent medium and is recycled to the process. This is a clear advantage over prior art methods where other inert solvents such as acetic acid were suggested and recovery thereof was imposed. The entire process is very simple to be carried out and requires standard equipment as used for these types of reactions. The reactor consists of an autoclave provided with a stirrer and condenser. The autoclave has a jacket through which heated oil or cooled water are circulated, the temperatures being controlled by a thermostat. The gaseous reactants are introduced through a sparger and the out-gases through a needle valve and flow meter. Samples can be drawn through a sampling valve. The reactants: toluene derivative, transition metal salt and phase transfer catalyst, are conveyed into the vessel followed by the introduction of air. The vessel is heated to about 130° C., whereby an increase of the pressure to about 15 atmospheres can be noticed. Upon the beginning of the reaction, the temperature increases to about 160° C. The evolving vapors containing toluene derivative and water, are condensed, the toluene derivative being recycled while the water is removed from the reaction system. After 2-3 hours, under continuous flow of air, the temperature drops by itself which indicates the end of the reaction. The further handling of the reaction products may be carried out in two different ways:

According to one embodiment the reaction product is distilled under vacuum. The residual distillate does contain the catalyst and could be recycled to a further cycle of toluene derivative oxidation. In this manner, the catalyst can be used a number of times, that is, one can for instance recover it together with the product of oxidation, separate out from the reactor, and utilize it again in the oxidation process.

According to another embodiment, an aqueous alkaline solution (15-30% by weight) is added to the cooled reaction product. Preferred alkaline compounds are sodium hydroxide, potassium hydroxide and ammonium hydroxide. The slurry is filtered and the separated solid comprising the catalyst is removed. The filtrate $ obtained is treated with a concentrated solution of an acid, preferably a mineral acid, whereby precipitated derivative of benzoic acid is separated. This second alternative will produce a benzoic acid derivative of a very high purity, even of above 99.%.

A person skilled in the art will select the proper mode of benzoic acid derivative separation and catalyst recovery according to the specific requirements and availabilities at site.

Of course, the entire process can be carried out in a continuous manner which has clear advantages from an industrial point of view.

While the invention will now be described in connection with certain preferred embodiments in the following Examples it will be understood that it is not intended to limit the invention to these particular embodiments. On the contrary it is intended to cover all alternatives, modifications and equivalents as may be included within the scope of the invention as defined by the appended claims. Thus the following Examples which include preferred embodiments will serve to illustrate the practice of this invention, it being understood that the particulars described are by way of example only and for purposes of illustrative discussion of preferred embodiments of the present invention.

In the Examples the concentrations and figures given are by weight unless otherwise stated.

Examples 17 and 18 do not illustrate the invention and are presented only for comparison purposes, to show the extent of conversion when phase-transfer catalysts not included in the claims of the present invention are used.

EXAMPLE 1

Preparation of p-chlorobenzoic acid

The equipment consisted of an autoclave (1 liter) equipped with a jacket and oil circulating thermostat, magnetic drived stirrer, water cooled condenser and liquid separator, sparger for introducing gaseous reactants, outlet for gas with a needle valve and flow meter and sampling valve.

The following reagents were introduced into the reactor: 180 g p-chlorotoluene, 5 g cobalt chloride-hydrate and 6.4 g of tetrahexyl ammonium bromide. The mixture was heated at about 137° C. under a pressure of 7.5 atmospheres of oxygen. The reaction was continued for about 5 hours, the temperature increasing to about 160° C. After cooling p-chlorobenzoic acid was separated at a yield of 99%.

EXAMPLE 2

Preparation of m-toluic acid

In the same equipment as in Example 1, the following reagents were introduced: 239 g of m-xylene, 1.1 of cobalt chloride-hydrate and 1.3 g of didecyldimethyl ammonium bromide. The mixture was heated to about 130° C. under a pressure of 15 atmospheres air (rate of 6 l/min). The reaction was continued for about 4 hours, the temperature increasing to about 160° C. The conversion as determined by gas chromatography (as in Example 3) was 90%. Meta-toluic acid was obtained by distillation at a yield of 97% having a purity of 99%.

EXAMPLE 3

Preparation of ortho-toluic acid

In the same equipment as in Example 1, the following reagents were introduced: 233 g of ortho-xylene (2.25 moles), 1.07 g of cobalt chloride hexahydrate (4.5 moles) and 1.8 g of tetraoctyl ammonium bromide (3.3 mmoles). The autoclave was heated to about 135° C. and pressure of about 10 atmospheres (air) was applied thereto. Air was allowed to skip at a flow rate of 2.0 l/min (STP).

The reaction mixture heated by itself and reached the temperature of about 170° C. being kept at this temperature for about three hours.

After cooling the mixture was distilled under vacuum (about 20 mm Hg) to yield 291 g of pure ortho-toluic acid (yield=95%).

EXAMPLE 4

Preparation of meta-toluic acid

The same procedure as in Example 3 was repeated using exactly the same amounts of reagents and reaction conditions, the only difference being the replacement of the ortho-xylene by meta-xylene.

The product obtained amounted to 281.5 g of pure metatoluic acid (92% yield).

EXAMPLE 5

Preparation of para-toluic acid

The same procedure as in Example 3 was repeated using exactly the same amounts of reagents and reaction conditions, the only difference being the replacement of the ortho-xylene by para-xylene. The product obtained consisted of 294 g of pure para-toluic, acid (96% yield).

EXAMPLE 6

Preparation of 4-chloro-benzoic acid

In the same equipment as in Example 1, the following reagents were introduced:

252 g of 4-chlorotoluene (2.25 moles); 1.02 g of cobalt chloride hexahydrate (4.5 mmoles) and 1.64 g of tetraoctyl ammonim bromide (3 mmoles).

The autoclave was heated at about 140° C. and pressure of about 15 atmospheres air introduced therein. Air was allowed to skip at a flow rate of 2.0 1/min (STP). After the reaction started, the temperature increased to about 162° C. After three hours, the temperature dropped to 140° C. indicating the end of the reaction. After cooling, the mixture was distilled under vacuum-(20 mm Hg) obtaining 330.9 g of pure 4-chloro-benzoic acid (94% yield).

EXAMPLE 7

Preparation of 4-nitrobenzoic acid

In the same equipment as in Example 1 the following reagents were introduced: 308 g of 4-nitrotoluene (2.25 moles);2.14, g of cobalt chloride hexahydrate (9.0 mmoles) and 2.6 g tetrahexyl ammonium bromide, (6 mmoles). Air pressure of 20 atmospheres was introduced in the autoclave.

After the reaction mixture was heated to about 150° C., air was allowed to skip from the autoclave at a rate of 2 1/min (STP). The reaction mixture heated by itself to about 170° C. and was kept at this temperature for about 4 hours.

After cooling the mixture was analyzed and found that reached a yield of 100% containing 46% moles of pure 4-nitrobenzoic acid in 4-nitrotoluene (54% moles) as the solvent medium. The 4-nitrotoluene was recycled to the oxidation step.

EXAMPLE 8

Preparation of 4-nitrobenzoic acid

The same experiment as in Example 7 was repeated using exactly the same reaction conditions and reagents, the only difference being the replacement of 2.6 g of tetrahexyl ammonium bromide by 3.3 g of tetraoctyl ammonium bromide (6 mmoles).

The final mixture consisted of 42% moles of pure 4-nitrobenzoic acid in 4-nitrotoluene (58% mole) as the solvent medium. 4-nitrotoluene was recycled to the oxidation step (total yield of 100% was achieved).

EXAMPLE 9

Preparation of p-phenyl benzoic acid

In the same equipment as in Example 1, the following reagents were introduced:

82.5 g of p-methyl diphenyl (2.25 moles); 1.07 g of cobalt chloride hexahydrate (4.5 mmoles) and 0.2 g of 20 didecyl ammonium bromide.

The autoclave was heated at about 140° C. and pressure of about 10 atmospheres air was introduced therein. Air was allowed to skip at a flow rate of 2 1/min (STP). After the reaction started, the temperature increased to about 165° C. After 3 hours at this temperature, the stirring was stopped. After cooling, the mixture was distilled under vacuum (20 mm Hg) obtaining 414 g of pure p-phenyl benzoic acid (92% yield).

EXAMPLE 10

Preparation of o-phenyl benzoic acid (diphenyl 2-carboxylic acid)

In the same equipment as in Example 1, the following reagents were introduced: 378 g of 2-methyl biphenyl; 1.1 g of cobalt chloride hydrate., and 1.3 g of didecyl ammonium bromide.

The autoclave was heated to about 140° C. and pressure of about 20 atmospheres air was introduced therein. Air was allowed to skip at a flow rate of 2 1/min (STP).

After the reaction started, the temperature increased to about 160° C. After 4 hours at this temperature, the stirring was stopped. After cooling, the mixture was analyzed and found to contain 396 g of diphenyl 2-carboxylic acid (89% yield).

EXAMPLE 11

Preparation of meta-toluic acid

In the same equipment as in Example 1, the following reagents were introduced:

238.5 g of meta-xylene; 5.6 g of chromium chloride hexahydrate (21 mmoles) and 9 g didecyl ammonium bromide (22.5 mmoles). The autoclave was heated and mixed for about 5 hours at 150° C. and pressure of about 16 atmospheres (air) being introduced therein at a constant flow of 2.3 1/min.

After cooling, the mixture was analyzed and found to contain 84% meta-toluic acid.

EXAMPLE 12

Preparation of ortho-toluic acid

In the same equipment as in Example 1, the following reagents were introduced:

238.5 g of ortho-xylene; 2,2 g of cobalt bromide hexahydrate (6.7 mmoles) and 2.23 g of tetra-n-hexyl-ammonium hydrogen sulfate.

The autoclave was heated and mixed for 5 hours to about 150° C. and pressure of about 20 atmospheres air being introduced therein with a constant flow of 3 1/min. After cooling, the mixture was distilled under vacuum to yield 281 g of ortho-toluic acid 91.8% yield) with a purity of 99%.

EXAMPLE 13

Preparation of para-chlorobenzoic acid

In the same equipment as in Example 1, the following reagens were introduced:

284.6 g of para-chlorotoluene; 1.6 g of cobalt chloride hexahydrate (6.7 mmoles) and 3.29 g of tetra-n-decylammonium bromide (5 mmoles).

The autoclave was heated and mixed to about 155° C. for 6 hours under a pressure of 20 atmospheres (air), being introduced therein at a constant flow of 3 1/min. After cooling, the mixture was distilled under vacuum to yield 318 g of para-chlorobenzoic acid (yield 90.3) with a purity of 99.9%.

EXAMPLE 14

Preparation of para-bromobenzoic acid

In the same equipment as in Example 1, the following reagents were introduced:

425.25 g of para-bromotoluene; 1.6 g of cobalt chloride hexahydrate (6.7 mmoles) and 2.25 g of tetrahexylphosphonium bromide.

The autoclave was heated and mixed for about 6 hours to 170° C. under a pressure of 17 atmospheres air with a flow of 2.2 l/min.

After cooling, the reacation mixture was analyzed by gas chromatography and found that the p-bromotoluene was selectively and completely converted into para-bromobenzoic acid.

EXAMPLE 15

Preparation of para-anisic acid

An amount of 0.82 g of n-hexyl bromide and 1.38 g of tri(n-hexyl)amine were dissolved in 10 g of para-methoxy toluene.

The solution was introduced into the autoclave (as in Example 1) together with 264.5 g of para-methoxytoluene and 1.6 g of cobalt chloride hexahydrate.

The mixture was heated and mixed at 140° C. for about 9 hours at a pressure of 15 atmospheres air (applied at a flow of 2 l/min).

After cooling the reaction mixture was found to contain 98% (mole) para-anisic acid and 2% of anisaldehyde.

EXAMPLE 16

Preparation of ortho-toluic acid

In the same equipment as in Example 1, the following reagents were introduced:

38.5 g of ortho-toluene; 2.2 g of cobalt bromide hexahydrate (6.7 mmoles) and 2.38 g of tetra-n-hexylammonium benzoate (5 mmoles).

The autoclave was heated and mixed for about 6 hours at 160° C. under air pressure of 16 atmospheres (applied at a flow of 2 l/min).

After cooling, the mixture was distilled under vacuum to yield 278.5 g or ortho-toluic acid (91% yield) with a purity of 99.1%.

EXAMPLE 17 (comparative example)

In the same equipment as in Example 1, the following reagents were introduced:

238.5 of para-xylene (2.25 moles); 1.6 of cobalt chloride hexahydrate and 1.6 g of tetra-n-butyl-ammonium bromide (5 mmoles).

The autoclave was heated for about 5 hours at 140° C. under air pressure of 15 atmospheres (applied at a flow of 2 l/min).

After cooling, the mixture was analyzed and found that it contained less than 5% of para-toluic acid the remaining being non-reacted para-xylene.

EXAMPLE 18 (comparative example)

In the same equipment as in Example 1, the following reagents were introduced:

238.5 g of meta-xylene (2.25 mmoles) 1.6 g of cobalt chloride hexahydrate (6.7 mmoles) and 2.45 g of tetra-n-hexylphosphonium iodide (5 mmoles).

The autoclave was heated and mixed for about 6 hours at 160° C. under air pressure of 20 atmospheres (applied at a flow of 3 l/min).

After cooling, the mixture was analyzed and found to contain less than 10% meta-toluic acid.

We claim:

1. A process for the manufacture of a derivative of benzoic acid from a toluene derivative by a liquid phase oxidation of said toluene derivative using an oxygen-containing gas, being carried out in the presence of a phase transfer catalyst selected from the group consisting of a quaternary onium salt and a crown ether, and traces of a polar solvent able to solubilize the catalyst, the polar solvent being water, the toluene derivative selected from the group consisting of a sulfonated toluene or an alkyl toluene, an aryl toluene, an aralkyl toluene, a halo-toluene, a nitrotoluene, an alkoxy toluene, an aryl-oxy toluene and combinations thereof, the process being characterized in that the oxidation reaction occurs in the presence of a catalytic system comprising:

(a) A quaternary onium salt having the general formula:

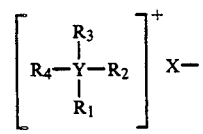

wherein: $R_1$ is alkyl and $R_2$, $R_3$ and $R_4$ may be the same or different, selected from an alkyl, a hydroxyalkyl, an aryl or an aralkyl group, $R_1$, $R_2$, $R_3$ and $R_4$ having a total number of carbon atoms from 17 to 58, Y may be nitrogen or phosphorus, and X is selected from $F^-$, $C^-$, $Br^-$, $OH^-$, $CH_3$, $COO^-$ and $HSO^-_4$ provided that when $BR^-$ is absent from the system a bromide or bromine is added;

(b) a transition metal salt, the molar ratio between (a) and (b) being from 0.25:1 to 1.5:1.

2. A process according to claim 1, wherein said quaternary onium salt is an ammonium or phosphonium salt having a total number of carbon atoms from 20 to 48.

3. A process according to claim 1, wherein the quaternary ammonium salt is formed in-situ.

4. A process according to claim 1, wherein the transition metal is selected from the groups 4 to 6 of the periodic Table.

5. A process according to claim 1, wherein said transition metal is selected from the group consisting of manganese, tungsten, mulybdenum, chromium, vanadium, cobalt, cerium or mixture thereof.

6. A process according to claim 5, wherein the anion bound to said transition metal is selected from chloride, bromide, acetate and sulfate or mixtures thereof.

7. A process according to claim 5, wherein said transition metal salt is hydrated cobalt chloride.

8. A process according to claim 1, wherein the molar ratio between the phase-transfer catalyst (a) and transition metal salt (b) is from 0.4:1 to 1.15:1.

9. A process according to claim 1, carried out at a temperature from 120° C. to 170° C.

10. A process according to claim 1, carried out at an oxygen partial pressure from 2 atmospheres to 5 atmospheres.

11. A process according to claim 1, further including that the oxidation reaction is carried out in the presence of a solvent.

12. A process according to claim 11, wherein said solvent is the starting toluene derivative compound.

13. A process according to claim 1, further including the step of treating the reaction product after cooling with a solution of metal alkali hydroxide producing a slurry from which the precipitate containing the catalyst is separated.

14. A process according to claim 13, wherein the metal alkali hydroxide is selected from sodium, potassium, and ammonium hydroxide or mixtures thereof.

15. A process according to claim 1, further including the step of distilling out the benzoic acid derivatives from the reaction product after cooling and recycling the catalyst to the process.

16. A process according to claim 1, wherein the derivative of benzoic acid is p-nitrobenzoic acid.

17. A process according to claim 1, wherein the derivative of benzoic acid is ortho-or para-halobenzoic acid.

18. A process according to claim 1, wherein the derivative of benzoic acid is meta-toluic acid.

19. A process according to claim 1, wherein the derivative of benzoic acid is ortho-toluic acid.

20. A process according to claim 1, wherein the derivative of benzoic acid is para-anisic acid.

21. A process according to claim 1, wherein the derivative of benzoic acid is para-bromo benzoic acid.

22. A process according to claim 1, wherein the derivative of benzoic acid is p-phenyl benzoic acid.

* * * * *